US00PP31660P2

(12) United States Plant Patent
Jarantoski

(10) Patent No.: US PP31,660 P2
(45) Date of Patent: Apr. 14, 2020

(54) ***VITEX* PLANT NAMED 'HELEN FROEHLICH'**

(50) Latin Name: *Vitex hybrida*
Varietal Denomination: HELEN FROEHLICH

(71) Applicant: Kris Jarantoski, Glencoe, IL (US)

(72) Inventor: Kris Jarantoski, Glencoe, IL (US)

(73) Assignee: Plants Nouveau llc, Mobile, AL (US)

( * ) Notice: Subject to any disclaimer, the term of this patent is extended or adjusted under 35 U.S.C. 154(b) by 0 days.

(21) Appl. No.: 16/501,081

(22) Filed: Feb. 19, 2019

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Vitex* hybrid cultivar named 'HELEN FROEHLICH' is disclosed, characterized by sterile flowers on compact, shrubby plants. Foliage is uniquely rounded. Flowers are large and held on dark peduncles. The new variety is a *Vitex* hybrid, typically used for ornamental outdoor purposes.

3 Drawing Sheets

Latin name of the genus and species: *Vitex hybrida.*
Variety denomination: 'HELEN FROEHLICH'.

BACKGROUND OF THE INVENTION

The new cultivar was discovered as part of a planned breeding program directed by the inventor, Kris Jarantoski. The parent varieties are unidentified, as the variety resulted from an open pollination and mass collected seed from breeding blocks including several varieties of *Vitex hybrida* plants. The seed parent is and unnamed, unpatented variety of *Vitex agnus-castus*. The pollen parent is an unnamed, unpatented variety of *Vitex rotundifolia*. This crossing was made during Summer of 1994. The new variety was selected September of 1995 at a botanic garden in Glencoe, Ill.

Asexual reproduction of the new cultivar 'HELEN FROEHLICH' by semi-softwood vegetative cuttings was first performed in July of 1998 at a research nursery in Glencoe, Ill. The inventor has confidentially reviewed plant performance over several years. Subsequent propagation has shown that the unique features of this cultivar are stable and reproduced true to type in successive generations. Date of first sale was Jul. 1, 2018, in the United States. This sale was made directly by the inventor or one who obtained the claimed invention directly or indirectly from the inventor. This sale and all public disclosures made before the filing of this application fall within the exception allowed under 102(b)(1).

SUMMARY OF THE INVENTION

The cultivar has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HELEN FROEHLICH'. These characteristics in combination distinguish 'HELEN FROEHLICH' as a new and distinct *Vitex* cultivar:

1. Sterile flowers.
2. Foliage can be simple or compound on the same plant.
3. Large flowers.
4. Compact, shrubby plant habit.
5. Dark peduncles.

PARENT COMPARISON

Plants of the new cultivar 'HELEN FROEHLICH' are similar to plants of the seed parent in most horticultural characteristics. However, plants of the new cultivar 'HELEN FROEHLICH' differ in the following characteristics;

1. Plants of the new variety produce both simple and compound foliage on the same plant, plants of the seed parent produce only compound foliage.
2. Flowers of the new variety are sterile, flowers of this comparator are fertile.

Plants of the new cultivar 'HELEN FROEHLICH' are similar to plants of the pollen parent in most horticultural characteristics. However, plants of the new cultivar 'HELEN FROEHLICH' differ in the following characteristics;

1. Plants of the new variety produce both simple and compound foliage on the same plant, plants of the pollen parent produce only compound foliage.
2. Flowers of the new variety are sterile, flowers of this comparator are fertile.
3. Terminal inflorescence of the new variety are longer than those of the pollen parent.

COMMERCIAL COMPARISON

Plants of the new cultivar 'HELEN FROEHLICH' are similar to plants of the commercial variety *Vitex agnus-*

*castus* 'Fletcher Pink', unpatented, in most horticultural characteristics. However, plants of the new cultivar 'HELEN FROEHLICH' differ in the following characteristics;

1. The new variety produces simple and compound leaves, this comparator produces only compound foliage.
2. The new variety produces lateral branches with maturity, producing an outwardly spreading plant. This comparator produces branches at the top of the plant, spreading upwardly.
3. Flowers of the new variety are sterile, flowers of this comparator are fertile.
4. Flowers of the new variety are violet colored, flowers of this comparator are rose-violet colored.

Plants of the new cultivar 'HELEN FROEHLICH' are also similar to plants of the commercial variety *Vitex agnus-castus* 'Le Compte', unpatented, in most horticultural characteristics. However, plants of the new cultivar 'HELEN FROEHLICH' differ in the following characteristics;

1. The new variety produces simple and compound leaves, 'Le Compte' produces only compound foliage.
2. The new variety produces lateral branches with maturity, producing an outwardly spreading plant. 'Le Compte' produces branches at the top of the plant, spreading upwardly.
3. Flowers of the new variety are sterile, flowers of 'Le Compte' are fertile.
4. Flowers of the new variety are violet colored, flowers of 'Le Compte' are rose-violet colored.

Plants of the new cultivar 'HELEN FROEHLICH' are also similar to plants of the commercial variety *Vitex hybrida* 'David Searle', U.S. Plant patent application Ser. No. 16/501,082 filed concurrently, in most horticultural characteristics. However, plants of the new cultivar 'HELEN FROEHLICH' differ in the following characteristics;

1. The new variety produces narrower foliage than 'David Searle'.
2. Inflorescences of the new variety are longer than those of 'David Searle'.
3. Plants of the new variety are approximately 20% larger at maturity in both height and width.

BRIEF DESCRIPTION OF THE PHOTOGRAPHS

The accompanying photograph in FIG. 1 illustrates in full color typical plants of 'HELEN FROEHLICH' grown outdoors in a trial field in Glencoe, Ill. The plants shown are approximately 4 years old.

Figure 1:
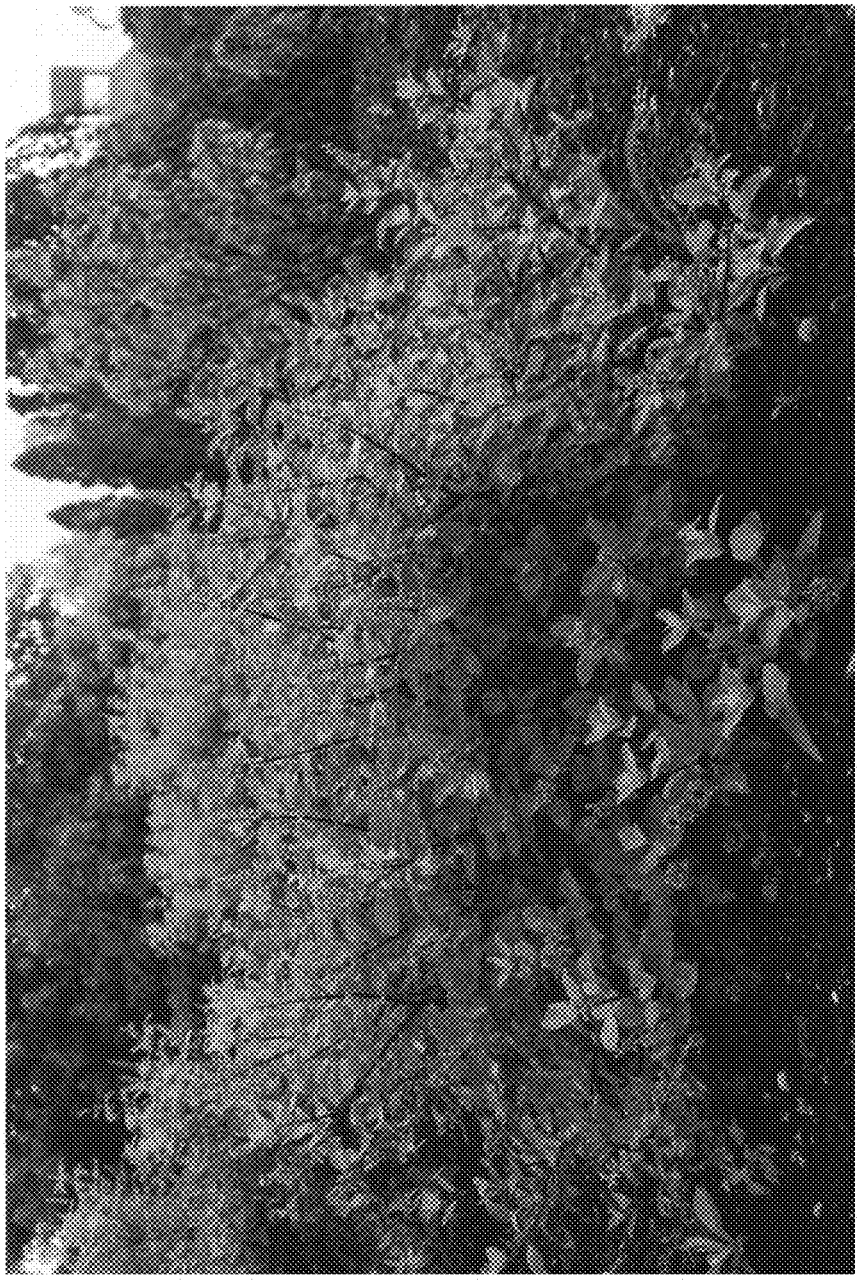
Figure 2:
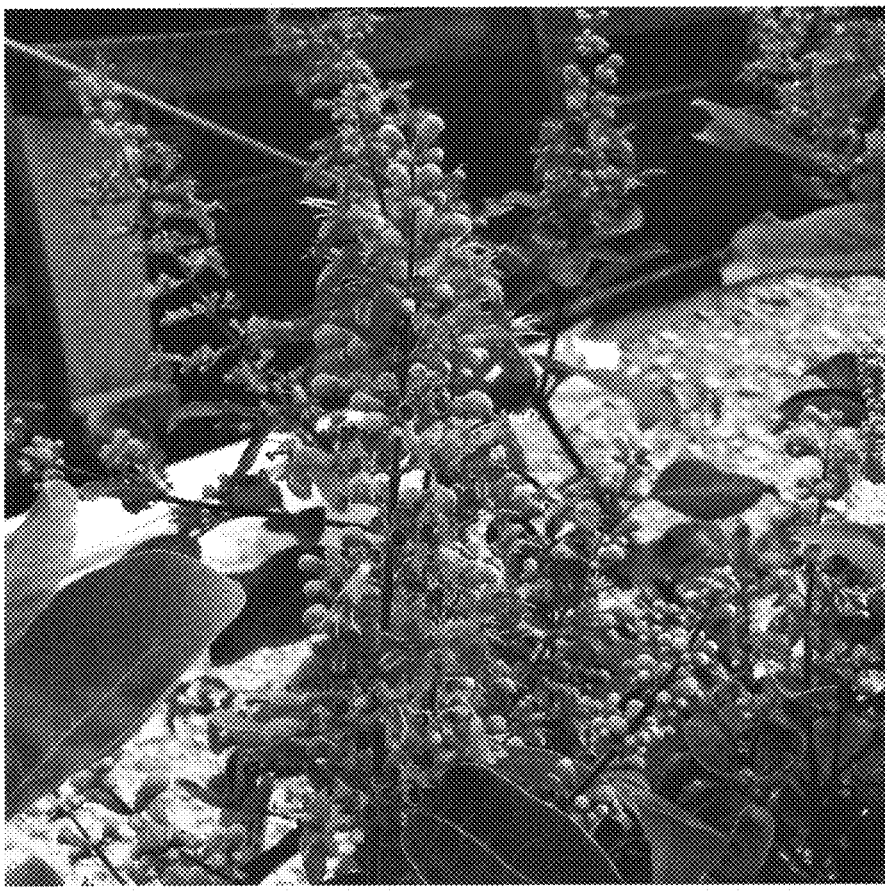
FIG. 2 illustrates a close up view of the inflorescence.
Figure 3:
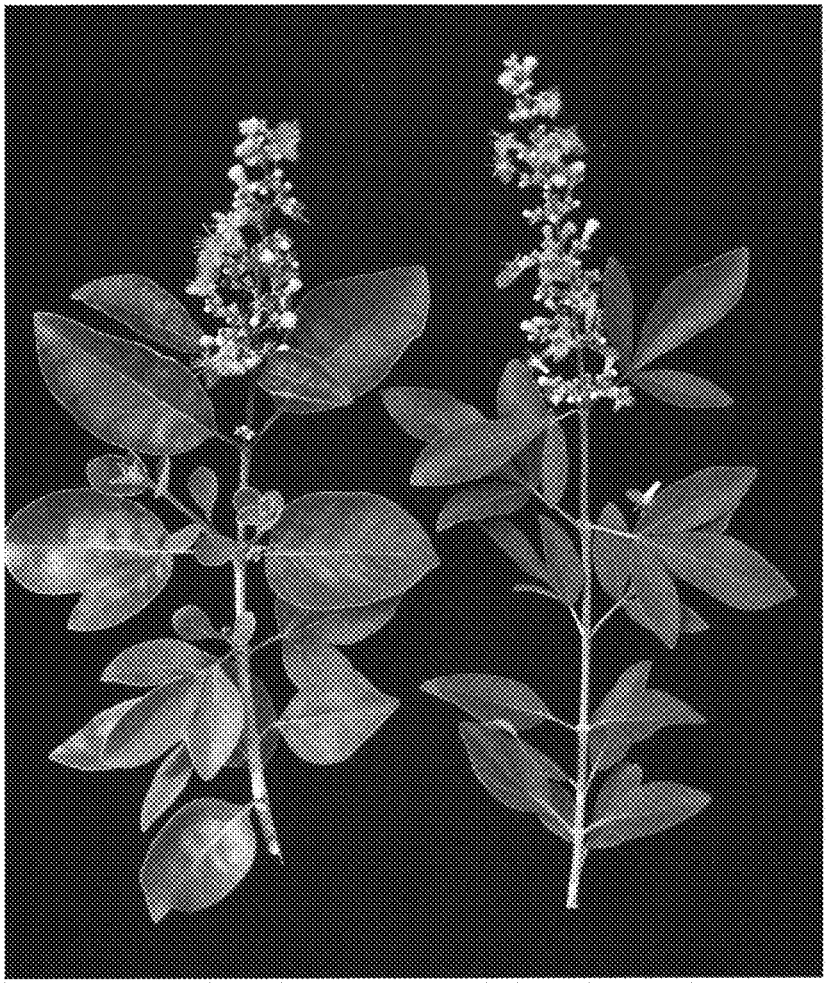
FIG. 3 illustrates inflorescence and foliage of the new variety on the right, and an inflorescence and foliage of the comparator 'David Searle' on the right.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 except where general terms of ordinary dictionary significance are used. The following observations and measurements describe 'HELEN FROEHLICH' plants grown outdoors in Southern California. Measurements and numerical values represent averages of typical flowering types.

Botanical classification: *Vitex hybrida* 'HELEN FROEHLICH'.

PROPAGATION

Time to rooting: Approximately 20 days at approximately 20° C.

Root description: Dense, free branching, thin, fibrous. Colored tan, not accurately measured with an R.H.S. chart.

Plant description:

Age of plant described: About 2 years in a 7 gallon container.

Growth habit: Perennial shrub. Outwardly branched, rounded.

Height: 75 cm in a 7 gallon container.

Width: 140 cm in a 7 gallon container.

Growth rate: Moderate to rapid.

Typical commercial container sizes: 3 to 15 gallon.

Branches:

*Branching habit.*—Freely branching.

*Lateral branch quantity.*—4 to 6 main lateral branches.

*Lateral branch length.*—35 to 55 cm.

*Lateral branch diameter.*—5 to 7 mm.

*Branch angle.*—Most branches 45 to 75 degrees from center.

*Branch strength.*—Strong.

*Branch color.*—Near RHS Brown 200C moderately covered in smooth striations colored near Greyed-Brown 197C.

*Internode length.*—Average range 2.5 to 4.0 cm.

Foliage:

Leaves:

*Arrangement.*—Opposite compound trifoliate or opposite simple.

*Length (excluding petiole).*—7.0 cm.

*Width.*—7.5 cm.

*Leaflet size.*—Center leaflet: 6.5 cm long, 3.5 cm wide. Lateral Leaflet: 4.5 cm long, 2.0 cm wide.

*Shape.*—Ovate.

*Apex.*—Acute.

*Base.*—Obtuse to broad tapered.

*Margin.*—Entire.

*Texture upper surface.*—Glabrous.

*Texture lower surface.*—Glabrous.

*Color.*—Immature: Upper: Near RHS Green 137A. Lower: Near Greyed-Green 190A. Mature: Upper: RHS Green 139A. Lower: RHS Greyed-Green 190B.

*Venation.*—Color: Upper: RHS Yellow-Green 144C. Lower: RHS Yellow-Green 145B.

Petiole:

*Length.*—5 mm.

*Width.*—1 mm.

*Texture.*—Some pubescence.

*Color.*—Upper side: RHS Yellow-Green 146D. Under side: RHS Yellow-Green 147D.

Inflorescence:

Description: Salverform flowers arranged in panicles.

Flowering season: Spring to Mid-Summer in Southern California.

Fragrance: None.

Number of flowers per inflorescence:

*Largest central panicles.*—Average range 100 to 140 on central.

*Lateral panicles.*—Average range 40 to 80.

Inflorescence height:
*Central panicle.*—12 to 18 cm.
*Lateral panicle.*—8 to 12 cm.
Inflorescence diameter:
*Central panicle.*—4 to 6 cm.
*Lateral panicle.*—4 to 5 cm.
Flowers:
*Flower diameter.*—1.5 cm.
*Flower length.*—1.1 cm.
*Flower throat diameter.*—4 mm.
*Flower tube diameter* (*base*).—2 mm.
*Flower tube length.*—8 mm.
*Flower angle.*—About 45°.
*Persistence.*—Self-Cleaning.
Flower bud:
*Length.*—8 mm.
*Diameter.*—5 mm.
*Shape.*—Obovate.
*Color.*—RHS Violet-Blue 94D, covered in 94C.
Individual flowers: The corolla is sympetalous and typically bilabiate with 2 small, highly fused lobes forming an upper lip and 3 larger highly fused lobes forming a lower lip.
Size:
*Upper lip.*—Diameter: Approximately 5 mm. Length: Approximately 5 mm.
*Lower lip.*—Length: Approximately 1 cm. Width: Approximately 8 mm.
Petals: One upper lip and one lower lip with 4 lobes. Lips are fused at base. All surfaces, including inner and outer tube are smooth and hairless.
*Tip shape.*—Upper lip: 2 rounded lobes. Lower lip: 2 rounded lobes.
Color:
*Upper lip.*—When opening: Inner surface: Near RHS Violet N88A. Outer surface: Near RHS Violet N88C. Fully opened: Inner surface: Near RHS Violet N88B. Outer surface: Near RHS Violet N88D. Fading: Inner surface: Near RHS Violet-Blue 90B. Outer surface: Near RHS Violet-Blue 91B flushed 92A.
Color:
*Lower lip.*—When opening: Inner surface: Near RHS Violet N88A, 2 center linear streaks near Violet 85D. Outer surface: Near RHS Violet N88C. Fully opened: Inner surface: Near RHS Violet N88B, 2 center linear streaks near White N155A. Outer surface: Near RHS Violet N88D. Fading: Inner surface: Near RHS Violet-Blue 90B, center linear streaks near White N155A. Outer surface: Near RHS Violet-Blue 91B flushed 92A.
Color:
*Tube.*—When opening: Inner surface: Near RHS Violet-Blue 91B. Outer surface: Near RHS Violet N88D. Fully opened: Inner surface: Near RHS Violet 85D flushed Violet 84C. Outer surface: Near RHS Violet-Blue 91C. Fading: Inner surface: Near RHS Violet 84D. Outer surface: Near RHS Violet 84D flushed Violet 84C.
Calyx: Sepals fused into a tube, tightly held around corolla.
Sepals:
*Shape.*—5 lobes entirely fused into a tube, except 1 mm acute lobes at apex.
*Length.*—Approximately 5 mm.
*Width.*—Approximately 4 mm.
*Margin.*—Entire.
*Texture.*—Slightly velvety.
*Color.*—Near RHS Greyed-Green 189C, flushed Greyed-Purple N187C.
Peduncle:
*Length.*—Average range 3 to 5 cm.
*Width.*—3 to 4 mm.
*Color.*—RHS Greyed-Purple N187B.
*Texture.*—Pubescent and ridged.
*Angle.*—Slightly outwardly curved.
*Strength.*—Strong.
Pedicels:
*Length.*—2 to 3 mm.
*Diameter.*—1 mm.
*Texture.*—Pubescent.
*Color.*—RHS Greyed-Green 190A.
*Strength.*—Good.
*Angle.*—About 45°.
Reproductive organs:
Stamens:
*Number.*—4.
*Filament length.*—Approximately 7 mm.
*Filament color.*—Near RHS Violet 84C.
Anthers:
*Shape.*—Obovate.
*Length.*—Approximately 2 mm.
*Color.*—Near RHS Violet 83A.
*Pollen.*—Not detected.
Pistil:
*Number.*—1.
*Length.*—Approximately 1.6 cm.
*Style.*—Length: Approximately 1.4 cm. Color: Near RHS Violet 84A.
*Stigma.*—Shape: 2-parted. Color: Near RHS Violet 86A. Ovary color: Near RHS Greyed-Green 191B.

OTHER CHARACTERISTICS

Disease and insect resistance: No significant disease or pest resistance nor susceptibility have been observed.
Temperature tolerance: USDA Zones 5-9.
Fruit/seed production: Fruit and seed production have not been observed in the new cultivar.

What is claimed is:

1. A new and distinct cultivar of *Vitex* plant named 'HELEN FROEHLICH' as herein illustrated and described.

* * * * *